United States Patent [19]

Gallopo et al.

[11] Patent Number: 5,616,314

[45] Date of Patent: Apr. 1, 1997

[54] QUATERNARY AMMONIUM ANTIBACTERIAL DENTIFRICES WITH SELECTED CALCIUM ABRASIVES

[75] Inventors: Andrew R. Gallopo, Garfield; Nader I. Ibrahim, Hackettstown; Salvatore Mazzanobile, Haworth, all of N.J.

[73] Assignee: SmithKline Beecham Corporation, Philadelphia, Pa.

[21] Appl. No.: 443,138

[22] Filed: May 17, 1995

Related U.S. Application Data

[63] Continuation of Ser. No. 129,191, Mar. 14, 1994, abandoned, which is a continuation of Ser. No. 683,149, Apr. 10, 1991, Pat. No. 5,176,901.

[51] Int. Cl.$^6$ ..................................................... A61K 7/16
[52] U.S. Cl. ............................................................. 424/49
[58] Field of Search ............................................ 424/49–88

[56] References Cited

U.S. PATENT DOCUMENTS

| | | | |
|---|---|---|---|
| 3,507,955 | 4/1970 | Osipow | 424/54 |
| 5,176,901 | 1/1993 | Gallopo et al. | 424/54 |

FOREIGN PATENT DOCUMENTS

| | | |
|---|---|---|
| 1126163 | 6/1982 | Canada . |
| 422803 | 4/1991 | European Pat. Off. . |
| 575137 | 12/1993 | European Pat. Off. . |
| 604158 | 6/1994 | European Pat. Off. . |
| 1194885 | 6/1970 | United Kingdom . |
| 9218096 | 10/1992 | WIPO . |

OTHER PUBLICATIONS

Chem. Abstracts 115:35524 (1991) of EP 422803 (Apr. 17, 1991).

*Primary Examiner*—Shep K. Rose
*Attorney, Agent, or Firm*—Dara L. Dinner; William T. King; Edward T. Lentz

[57] ABSTRACT

Dentrifices containing cationic antibacterial agents are disclosed herein.

4 Claims, No Drawings

QUATERNARY AMMONIUM ANTIBACTERIAL DENTIFRICES WITH SELECTED CALCIUM ABRASIVES

This is a continuation of application Ser. No. 08/129,191, filed Mar. 14, 1994, now abandoned, which is a continuation of application Ser. No. 07/683,149, filed Apr. 10, 1991, now U.S. Pat. No. 5,176,901.

BACKGROUND OF THE INVENTION

The present invention relates to a dentifrice comprising a cationic antibacterial agent useful in the prophylaxis and/or treatment of periodontal disease, calculus and caries and selected abrasives. A new thickening agent comprising a soluble alkali metal pyrophosphate and a calcium salt is also disclosed.

The use of antibacterial agents, including cationic antibacterial agents, in oral hygiene compositions has been widely advocated as a means of reducing the bacterial plaque population and this may be beneficial in the treatment of periodontal disease, calculus and/or caries.

While mouthwashes containing cationic antibacterial agents are available, these suffer the disadvantage that the cationic antibacterial agents tend to leave a brown stain due to interaction of the agents with plaque. Such a drawback may be, in principle, minimized by using the antibacterial agent in a dentifrice, so that the abrasive included therein removes the stained plaque. In practice however there are found to be severe problems in providing a useful formulation because of the intrinsic incompatibility of the cationic antibacterial agents with many of the other conventional elements of a dentifrice formulation, which incompatibility drastically reduces the bio-availability of the cationic agent. In addition, the cationic antibacterial agents often have a bitter taste which needs to be masked to provide a produce which is acceptable to the consumer.

It has now been discovered that the problem of bio-availability may be overcome or at least mitigated by the use of certain abrasives in combination with cationic antibacterial agents in dentifrices. Also, the thickening agents based on a pyrophosphate and a calcium salt make i% possible to eliminate all or essentially all of certain thickening agents such as non-abrasive silica gels which may reduce CPC availability.

SUMMARY OF THE INVENTION

Accordingly, the present invention provides a dentifrice for reducing plaque formation and treating gingivitis on teeth and soft tissue comprising:

(a) an amount of a cationic antibacterial agent sufficient to usefully reduce plaque formation and treat gingivitis;

(b) at least one thickening agent which is not an anionic thickening agent;

(c) at least one surfactant which is not an anionic surfactant; and (d) a non-silica abrasive which is essentially insoluble in said dentifrice.

Another aspect of this invention is that it has been found these and other dentifrice can be thickened by combining a soluble or sparingly soluble alkali metal pyrophosphate with an insoluble or essentially insoluble calcium salt thereby creating in situ material which thickens dentifrice formulations.

Optionally a humectant, an anti-caries agent, flavoring agents and other excipients necessary or useful in formulating and using a dentifrice can be included in these compositions.

SPECIFIC EMBODIMENTS

These dentifrice may be substantially solid, pasty or liquid in character such as is found in a tooth powder, a denial tablet or a toothpaste or dental cream. These compositions typically will have a pH similar to that of the oral cavity, but may be formulated so as to be either acidic or alkaline. Buffers may be added to maintain pH if desired. A preferred pH range for these toothpastes is between 6 and 8.

Suitable cationic antibacterial agents for use in dentifrices of the invention include:

(i) quaternary ammonium compounds, for instance those in which one or two of the substituents on the quaternary nitrogen has between 8 and 20, preferably 10 and 18 carbon atoms and is preferably an alkyl group, which may optionally be interrupted by an amide, ester, oxygen, sulphur, or heterocyclic ring. The remaining nitrogen substituents will have a lower number of carbon atoms, for instance between 1 and 7, and are preferably alkyl, for instance methyl or ethyl, or benzyl. The anion will be an orally acceptable salt forming group. Examples of such compounds including benzalkonium, chloride, dodecyl trimethyl ammonium chloride, benzyl dimethyl stearyl ammonium chloride, and cetyl trimethyl ammonium bromide, benzethonium chloride (diisobutyl phenoxyethoxyethyl dimethylbenzyl ammonium chloride), and methyl benzethonium chloride;

ii) pyridinium and isoquinolinium compounds, exemplified by hexadecylpyridinium chloride, cetyl pyridinium chloride, and alkyl isoquinolinium bromide;

(iii) pyrimidine derivatives such as hexetidine (5-amino-1,3-bis(2-ethylhexyl)-5-methylhexahydropyrimidine);

(iv) amidine derivatives such as hexamidine isethionate (4,4'-diamidino-α,ω-diphenoxyhexane isothionate);

(v) bispyridine derivatives such as octenidine (N,N'[1,10-decanediyldi-1(4H)-pyridinyl-4-ylidene]bis(1-octanamine dihydrochloride); and (vi) biguanides including:

(a) mono-biguanides such as p-chlorobenzyl biguanide, and N'-(4-chlorobenzyl)-N''-(2,4-dichlorobenzyl) biguanide.

(b) bis-biguanides of the general formula (I):

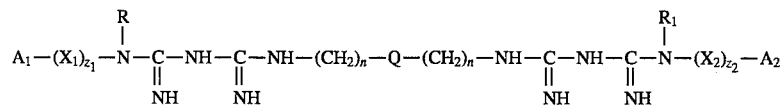

wherein:

$A_1$ and $A_2$ are independently a phenyl group optionally substituted by $(C_{1-4})$alkyl, $(C_{1-4})$alkoxy, nitro, halogen, $C_{1-12}$)alkyl group, or $(C_{4-12})$alicylclic;

$X_1$ and $X_2$ are independently $(C_{1-3})$alkalene;

R and $R^1$ are independently hydrogen, $(C_{1-12})$alkyl, or aryl$(C_{1-6})$alkyl;

$Z_1$ and $Z_2$ are independently 0 or 1;

Q is $CH_2$, oxygen, sulfur, or aryl;

n in each $(CH_2)_n$ group is independently is an integer from 1 to 12 but the total of both n groups may not exceed 12;

aryl is phenyl, naphthyl or another aromatic ring; and orally acceptable acid addition salts thereof. Preferred compounds are chlorhexidine and alexidine. (c) poly(biguanides) such as polyhexamethylene biguanide hydrochloride.

An amount sufficient of the cationic antibacterial agent to usefully reduce plaque formation and treat gingivitis will be one in the range of about 0.005 to 10% weight/weight (w/w), preferably 0.005 to 5%, more preferably 0.005 to 2.5% and most preferably 1.0% w/w.

Any thickening agent may be used so long as it is not an anionic thickening agent. More specifically, nonionic and cationic thickening agents are preferred for use in this invention.

Suitable nonionic thickening agents include $(C_{2-6})$alkylene oxide modified $(C_{1-6})$alkylcellulose ethers, for instance hydroxyethylcellulose, hydroxypropylcellulose, hydroxypropylmethylcellulose, and mixtures thereof.

Suitable cationic thickening agents include quaternary cellulose derivatives such as the products supplied by Amerchol Europe under the trademark LR 30M and JR 30M, cationic guar gum derivatives such as the products supplied by Celanse under the trademark Jaguar C17 (guar hydroxypropyltriammonium chloride), or a copolymer of a diallyl ammonium chloride and acrylic acid such as the product supplied by Merck and Co. under the trademark 'Merquat 280' (CFTA approved name polyquaterinium 22). Other thickening agents which may be employed include polyvinylpyrrolidone, starch and certain non-abrasive silica gels such as those sold by Huber under the trade name Zeofree, and other silica thickening agents.

Advantageously thickening agent are present in the range 0.01 to 30% preferably 0.1 to 15%.

The thickening agent aspect of this invention is achieved by combining a soluble or sparingly soluble alkali metal pyrophosphate with an insoluble or essentially insoluble calcium salt and thereby creating in situ material which thickens dentifrices. Useful soluble alkali metal pyrophosphates are, for example, tetrasodium and tetrapotassium pyrophosphate or combinations thereof. Calcium salts which can be used in combination with the those pyrophosphates are, for example, $CaCO_3$, $CaHPO_4$ and the like. Useful concentrations of the soluble pyrophosphate range up to about 10.0% of the composition by weight, preferably up to about 8% by weight. As for the calcium salt, it is expected that some amount in the range of up to 3.0%, preferably 0.5 to 2.6% by weight, will impart a thickening affect to a dentifrices. If a calcium salt is used as the abrasive, thickening is achieved without reducing the abrasive characteristics of the formulation by increasing the amount of that abrasive salt-by several percentage points, for example 1 to 2%.

Any surfactant may be used in this invention so long as it is not anionic. For example nonionic, cationic and amphoteric surfactants may be used in these dentifrices.

Suitable nonionic surfactant include polyethoxylated sorbitol monoesters (for instance, the products marketed under the trade name 'Tween' by ICI); polycondensates of ethylene oxide and propylene oxide (poloxamers) (for instance the products marketed under the trade name 'Plutonic' by BASF-Wyandotte); condensates of propylene glycol and polyethoxylated hydrogenated castor oil (for instance, cremophors).

Suitable amphoteric surfactants include long chain imidazoline derivatives such as the product marketed under the trade name 'Miranol C2M' by Miranol; long chain alkyl betaines, such as the product marketed under the trade name 'Empigen BB' by Albright & Wilson; and long chain alkyl amidoalkyl betaines, such as cocamidopropylbetaine, and mixtures thereof.

Useful cationic surfactants may be, for example, cocamidopropyl PG dimonium chloride phosphate (Monaquat PTC) and lauramidopropyl PG dimonium chloride phosphate (Monaquat PTL).

These dentifrices contain abrasives, also called polishing materials. For the purposes of this invention, essentially insoluble abrasives are to be used. The term insoluble is defined with reference to both the confected dentifrices and its use in the oral cavity.

Examples of such abrasives are certain phosphates such as sodium metaphosphate, potassium metaphosphate, tricalcium phosphate, dicalcium phosphate dihydrate, anyhdrous dicalcium phosphate, calcium pyrophosphate, zinc orthophosphate, alumina, hydrated alumina, aluminum silicate, bentonite, certain carbonates such as calcium carbonate, and mixtures thereof. Preferred abrasives include dicalcium phosphate, particularly the dihydrate, calcium pyrophosphate, calcium carbonate and alumina.

Most if not all of the abrasives listed above available from commercial sources, or they can be prepared by means known in the art. For instance, dicalcium phosphate in the preferred dihydrate form is readily available from many commercial sources. Likewise calci pyrophosphate and calcium carbonate are commercially available. If alumina is used, and there are many sources, it is most preferred to use a hydrated alumina such as that sold by Alcoa as C333. It is understood that any chosen abrasive will be sufficiently pure so as to meet the health and regulatory standards for a dentifrices.

Abrasives are generally present in amounts ranging from about 5% to about 95% by weight of the oral preparation. Preferably, they will be present in amounts ranging from about 5% to about 75% in toothpaste and from about 10% to about 95% in tooth powder.

In certain forms of this invention a fluoride-providing compound is present in the oral preparation. These compounds may be slightly soluble in water or may be fully water-soluble. They are characterized by their ability to release fluoride ions in water and by substantial freedom from reaction with other compounds of the oral preparation. Among these materials are inorganic fluoride salts, such as soluble alkali metal, alkaline earth metal and heavy metal salts, for example, sodium fluoride, potassium fluoride, ammonium fluoride, lead fluoride, a copper fluoride such as cuprous fluoride, zinc fluoride, a tin fluoride such as stannic fluoride or stannous chlorofluoride, barium fluoride, sodium fluorosilicate, ammonium fluorosilicate, sodium fluorozirconate, sodium monofluorophosphate, aluminum mono- and difluorophosphate, and fluorinated sodium calcium pyrophosphate. Alkali metal and tin fluorides, such as sodium and stannous fluorides, sodium monofluorophosphate and mixtures thereof, are preferred.

The amount of the fluoride-providing compound is dependent to some extent upon the type of compound, its solubility and the type of oral preparation, but it must be a nontoxic amount. In a solid oral preparation, such as a toothpaste or tooth powder, an amount of such compound which releases a maximum of 1% by weight of the preparation is considered satisfactory. Any suitable minimum amount of such compound may be used, but it is preferable to employ sufficient compound to release from 0.005% to 2%, and preferably about 0.1% of fluoride ion. Typically, in the cases of alkali metal fluorides and stannous fluoride, the component is present in an amount up to 4% by weight, based on the weight of the preparation, and preferably in the range of from 0.05% to 2%. In the case of sodium monofluorophospate (MFP), the compound may be present in an amount up to 7.6% by weight more typically 0.76%.

Optionally, anti-calculus agents may be incorporated into these compositions. For example certain pyrophosphates have been found to be useful in reducing calculus formation. There are numerous publications and patents describing pyrophosphate-based anti-calculus compositions and their use in the oral cavity. For example see U.S. Pat. No. 3,515,772 which describes the use of certain alkali metal pyrophosphates, particularly di alkali and tetra-alkali metal pyrophosphate salts of $P_2O_7^{-4}$. The tetrapotassium and tetrasodium forms are most frequently used in dentifrices as anticalculus agent. This U.S. patent is incorporated herein by reference as if set out in full in this writing. Other phosphates, including hexametaphosphates, tripolyphosphates and other polyphosphates, usually in the form of an alkali metal salt, have been proposed or are being used in dentifrices as anticalculus agents. It is expected that one or more of these agents can be usefully incorporated into the compositions of this invention.

In preparing tooth powders, it is usually sufficient to admix mechanically, e.g., by milling, the various solid ingredients in appropriate quantities and particle sizes.

With regard to pastes the liquid vehicle may comprise water, and usually a humectant, typically in an amount ranging from about 10% to about 90% by weight of the preparation. Glycerin, sorbitol, or polyethylene glycol are examples of useful humectants. Particularly advantageous liquid ingredients comprise mixtures of water, glycerine or sorbitol.

Various other ingredients such as preservatives, dyes ant other coloring agents, flavorings, sweeteners, anti-staining agents, desensitizing agents and the like may be added to these dentifrices. Such additives are frequently used in dentifrices and are therefore well known in the art.

It will be understood that these dentifrices are to be sold or otherwise distributed in suitably labelled packages. Toothpastes are packaged in tubes or squeezable tubes (aluminum or plastic) or containers or in a rigid tube with some expelling device for delivering the paste, such as a pump. Powders normally are prepared in cans or bottles with a removable top or some means whereby the powder can be dispensed by inverting and shaking or by introducing a spoon or other device for removing a portion of the powder. Liquid formulations can be packaged in capped tubes or bottles and be dispensed by squeezing, mechanical means; pre-pressurized containers may also used with liquid formulations.

This invention is further illustrated by the following examples. These examples are only intended to illustrate the invention not to limit its scope or practice in any manner or form. Formulations are given on a weight/weight basis.

EXAMPLES 1

CPC/Dicalcium Phosphate Abrasive Toothpaste

An example of a toothpaste where the abrasive is dicalcium phosphate dihydrate is set out below. Table I lists the ingredients for the paste, which was tested for the availability of the cationic antibacterial by extracting the water solubles, then looking at the amount of recovered antibacterial via instrumental analyses such as an HPLC-bases assay and microbiological assay.

TABLE 1

| Ingredients | Percent by Weight/Weight |
|---|---|
| Glycerin | 7.000 |
| Methocel KI5M[1] | 0.600 |
| Na MFP | 0.836 |
| Na Saccharin | 0.246 |
| Sorbitol | 3.550 |
| CaHPO$_4$ Dihydrate | 40.000 |
| TiO$_2$ | 0.956 |
| Flavor | 0.800 |
| Deionized Water | 36.012 |
| Pluronic F127 | 9.000 |
| CPC[2] | 1.000 |
| | 100.000 |

[1]Hydroxymethylpropylcellulose, Dow Chemical Co.
[2]Cetylpyridinium chloride.

A paste suitable for use as a dentifrice using these materials was prepared as follows: The glycerin and Methocel were mixed together. Then the sodium monofluorophosphate and sodium saccharin were dissolved in a portion of the water and added to the first mix. Sorbitol (Sorbo) was then added, followed by a mix of the dicalcium phosphate dihydrate and titanium dioxide. Flavoring was then added after which a mixture of the remaining water, Pluronics and CPC was mixed into the earlier prepared mixture.

EXAMPLE 2

CPC/Alumina Abrasive Toothpaste

A toothpaste with alumina as the abrasive and CPC as the cationic antibacterial agent was prepared. Table II sets out the ingredients and their relative amounts.

TABLE II

| Ingredients | Percent by Weight/Weight |
|---|---|
| Glycerin | 20.000 |
| Natrosol 250 H[3] | 1.000 |
| Na MFP | 0.836 |
| Na Saccharin | 0.246 |
| Alumina | 14.000 |
| Zeofree 153[4] | 10.000 |
| TiO$_2$ | 0.956 |
| PEG 400 | 3.000 |
| Flavor | 0.800 |
| Deionized Water | 46.162 |
| Pluronic F-87 | 1.000 |
| Pluronic F-127 | 1.000 |
| CPC | 1.000 |
| | 100.00% |

[3]Hydroxyethyl cellulose, Aqualon.
[4]Thickening silica, Huber.

The paste was prepared by first combining glycerin and the Natrosol 250H in a portion of the water. To this was added a mix of water, the sodium monofluorophosphate and sodium saccharin. Then alumina, Zeofree 153 and titanium dioxide was combined and added to the existing mixture. A mix of the remaining glycerin and PEG 400 was added followed by the flavoring agent. Finally the rest of the water mixed with the Pluronics and CPC was added with mixing to form a toothpaste.

EXAMPLE 3

CPC/Alumina Toothpaste with Pyrophosphates

A paste with pyrophosphates for tartar removal was prepared with the CPC/alumina paste of Example 2. Table III recites the ingredients and amounts contained in this preparation.

TABLE III

| Ingredients | Percent by Weight/Weight |
|---|---|
| Na MFP | 0.836 |
| Na Saccharin | 0.246 |
| $K_4P_2O_7$ | 4.000 |
| $Na_4P_2O_7$ | 1.810 |
| Alumina | 14.000 |
| Zeofree 153 | 10.000 |
| $TiO_2$ | 0.956 |
| Glycerin | 20.000 |
| PEG 400 | 3.000 |
| Flavor | 0.800 |
| Deionized Water | 40.352 |
| Pluronic F-127 | 1.000 |
| Pluronic F-87 | 1.000 |
| CPC | 1.000 |
| | 100.000 |

A paste was prepared from these materials in the manner described in Example 2.

EXAMPLE 4

CPC/Calcium Pyrophosphate Toothpaste

Toothpastes with calcium pyrophosphate as the abrasive were prepared. Table V gives a representative example of the ingredients which were used to prepare such pastes.

TABLE IV

| Ingredients | Percent by Weight/Weight |
|---|---|
| $K_4P_2O_7$ | 5.000 |
| $Na_4P_2O_7$ | 1.810 |
| Na MFP | 0.836 |
| Na Saccharin | 0.246 |
| $CaHPO_4$ | 2.300 |
| Glycerin | 22.000 |
| Natrosol 250H | 0.600 |
| Calcium pyrophosphate | 40.000 |
| $TiO_2$ | 0.956 |
| Flavor | 0.800 |
| Pluronic F-127 | 1.000 |
| Pluronic F-87 | 1.000 |
| CPC | 1.000 |
| Deionized Water | quo 100% |

In making up a paste, a portion of the water was used to dissolve up the pyrophosphates, sodium monofluorophosphate and sodium saccharin. Then the dicalcium phosphate was added to that mix. Subsequently, a portion of the glycerin and Natrosol 250H were combined and mixed in with earlier mixture. A mix of calcium pyrophosphate and titanium dioxide was then prepared and incorporated into the earlier mix. The remaining glycerin was then added, followed by the flavoring agent. Finally, a mixture of water, pluronics and CPC was prepared and mixed in with the previously described mixture to form the paste.

EXAMPLE 5

CPC/Calcium Carbonate Toothpaste

Toothpastes with calcium carbonate as the abrasive were prepared. Table IV gives a representative example of the ingredients where used to prepare such pastes.

TABLE V

| Ingredients | Percent by Weight/Weight |
|---|---|
| Natrosol 250 H | 1.500 |
| Na MFP | 0.836 |
| Na Saccharin | 0.246 |
| Zeofree 153 | 5.000 |
| Glycerin | 22.000 |
| $CaCO_3$ | 35.000 |
| $TiO_2$ | 0.956 |
| Flavor | 0.800 |
| Pluronic F-127 | 1.000 |
| Pluronic F-87 | 1.000 |
| CPC | 1.000 |
| Deionized Water | quo 100% |

Here, qs refers to a quantity sufficient to make 100%. The order of mixing was as follows: Part of the glycerin, part of the water and Natrosol 250H were combined. To this was added a mixture comprising water, sodium monofluorophosphate and sodium saccharin. Calcium carbonate was added to this mixture. The remaining glycerin was then added followed by a mixture of the Zeofree and the titanium dioxide. Flavoring was added followed by a mix of the Pluronics and CPC.

What is claimed is:

1. A process for thickening a dentifrice formulation which comprises an alkali pyrophosphate, a cationic antibacterial agent, and a calcium salt, the improvement comprising combining, in water, a soluble or sparingly soluble alkali metal pyrophosphate with an insoluble or essentially insoluble calcium salt in situ, which thickens said dentifrice formulation, without adding a thickening agent.

2. The process according to claim 1 where the alkali metal pyrophosphate is tetrasodium or tetrapotassium pyrophosphate.

3. The process according to claim 2 where the calcium salt is calcium carbonate, or calcium pyrophosphate.

4. The process according to claim 3 where the alkali metal is present in an amount up to about 10.0% and the calcium salt is present in an amount up to 3.0%.

* * * * *